(12) United States Patent
Laurent et al.

(10) Patent No.: US 6,177,416 B1
(45) Date of Patent: Jan. 23, 2001

(54) OXYIMINOPREGNANCARBOLACTONES

(75) Inventors: Henry Laurent; Ralph Lipp; Peter Esperling; Johannes-Wilhelm Tack, all of Berlin (DE)

(73) Assignee: Schering Aktiengesellschaft (DE)

( * ) Notice: Under 35 U.S.C. 154(b), the term of this patent shall be extended for 0 days.

(21) Appl. No.: 09/308,992

(22) PCT Filed: Dec. 1, 1997

(86) PCT No.: PCT/EP97/06657

§ 371 Date: Oct. 5, 1999

§ 102(e) Date: Oct. 5, 1999

(87) PCT Pub. No.: WO98/24801

PCT Pub. Date: Jun. 11, 1998

(30) Foreign Application Priority Data

Dec. 1, 1996 (DE) ............................................. 196 51 000

(51) Int. Cl.[7] ........................ A61K 31/585; A61K 31/56; C07J 21/00

(52) U.S. Cl. .............................. 514/175; 540/41; 540/44; 540/170

(58) Field of Search .......................... 540/44, 41; 514/175

(56) References Cited

U.S. PATENT DOCUMENTS 4,129,564 * 12/1978 Wiechert et al. ................ 260/239.57
5,569,652 * 10/1996 Beier et al. ........................... 514/173

FOREIGN PATENT DOCUMENTS

2652761 * 3/1978 (DE) .
3022337 * 1/1982 (DE) .
3916112 * 11/1990 (DE) .
0709394 * 3/1996 (EP) .

OTHER PUBLICATIONS

Chemical Abstracts, vol. 099, No. 7, Aug. 15, 1983, Columbus, Ohio, US: abstract No. 054065, Moravcsik I et al: "Steroid oxime" XP002061595, siehe Zusammenfassung & Hu 23 286 0 (Gyogyszerkutato Intezet; Hung.) Aug. 30, 1982.*

* cited by examiner

*Primary Examiner*—Barbara Badio
(74) *Attorney, Agent, or Firm*—Millen, White, Zelano & Branigan, P.C.

(57) ABSTRACT

3-Oxyiminopregnane-21-carbolactones of formula I,

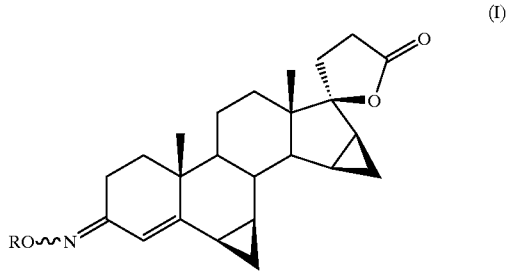

wherein R is as defined by the specification, their production and use as pharmaceutical agents are described.

23 Claims, No Drawings

OXYIMINOPREGNANCARBOLACTONES

This application is a 371 of PCT/EP97/06657 filed Dec. 1, 1997.

This application claims the benefit of the filing date of U.S. Provisional Application Ser. No. 60/034,997 filed Jan. 7, 1997.

The invention relates to the new oxyiminopregnanecarbolactones of general formula I, a process for their production, pharmaceutical preparations that contain these oxyiminopregnanecarbolactones, as well as their use for the production of pharmaceutical agents.

The invention relates to the (E,Z)-mixtures and the isomer-pure (E) and (Z) compounds of formula I,

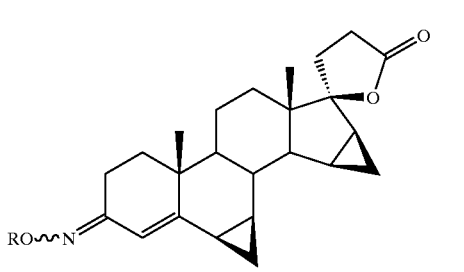

(I)

in which

R means a hydrogen atom or an acyl radical with 2 to 10 C atoms.

As an acyl radical R, a radical C(O)R', in which R' is a hydrocarbon radical that is straight-chain or branched-chain or cyclic, saturated, or unsaturated in up to three places; an alkylcycloalkyl or cycloalkenyl radical, in each case with up to 9 carbon atoms; or a benzoyl radical, is suitable.

Preferred radicals for R are either the hydrogen atom or a more linear, saturated alkanoyl radical with 2 to 10 carbon atoms, i.e., R' is a methyl, ethyl, propyl, butyl, pentyl, hexyl, hepty, octyl, or nonyl group.

As a branched-chain, saturated hydrocarbon radical, for example, the i-propyl or t-butyl radical can be cited.

As a cyclic hydrocarbon radical, primarily the cyclopropyl, cyclopentyl, or cyclohexyl radicals are suitable.

The methylcyclopropyl, methylcyclohexyl, or methylcyclohexenyl radicals can be cited as representatives of an alkylcycloalkyl or cycloalkenyl radical.

The 3-keto compound of formula II (drospirenone) that is analogous to the compounds of general formula I

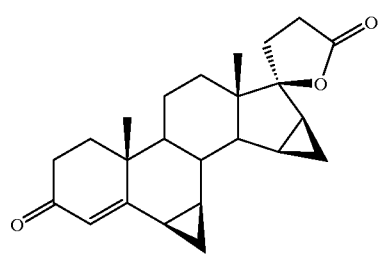

(II)

is described as a compound with a) an anti-aldosteronic action (DE-A 26 52 761)

b) a gestagenic action (DE-A 30 22 337), as well as c) a strong antiandrogenic action, and this at a dosage that is sufficient for contraception (DE-A 39 16 112).

Drospirenone is the first synthetic gestagen which, like natural progesterone, exhibits all three partial actions a), b), and c), in a common dose range, but unlike progesterone is also bio-available in a relevant amount after oral administration. Drospirenone can therefore be used either by itself or preferably in combination preparations together with an estrogen for hormonal contraception and/or for hormone replacement therapy. Owing to the antimineralocorticoids and antiandrogenic partial action, these preparations are also suitable for users for whom hormonal combination preparations are otherwise contraindicated (DE-A 39 16 112).

The required daily dose of drospirenone for contraception or hormone replacement therapy is 1 to 10 mg.

For some time now, transdermal administration as well as subcutaneous administration by so-called implants of hormonal active ingredients has been of great interest for hormone replacement therapy and recently also for contraception (Te-Yen Chien et al., "Transdermal Contraceptive Delivery System: Preclinical Development and Clinical Assessment" in Drug Development and Industrial Pharmacy, 20(4), 633–664 (1994)).

To date, drospirenone's disadvantageous physicochemical substance properties, such as, e.g., low solubility in organic polymers, has hampered reasonable use of it via the last-mentioned routes of administration.

The object of this invention therefore consists in converting drospirenone into derivatives that are to have considerably improved physicochemical substance properties, without the very advantageous pharmacological profile being significantly altered.

It has now been found that this can be achieved by converting drospirenone into the 3-oxime derivative (R=H) or the corresponding O-acyl derivative (R=acyl) of general formula I. The derivatives of general formula I are distinguished by, surprisingly enough, several times greater solubility than drospirenone in organic polymers, which are suitable as skin contact adhesives, such as, e.g., polyacrylates, silicone adhesives, synthetic rubber). In the case of transdermal administration, only this greatly increased solubility permits the release of the intact prodrug of general formula I from the matrix in an amount that can ensure an adequate transdermal flow of the active compound (drospirenone) or else its prodrug (compound of general formula I). This is in turn a prerequisite for a more relevant active ingredient level in the serum actually to be brought about.

The compounds thus are the first to actually make it possible to take full advantage of the contraceptive or therapeutic action of drospirenone after transdermal administration of a prodrug. Just like drospirenone itself, they can also be given orally, however.

Contraceptively effective 3-oximes and O-acylates have already been described in the 19-nortestosterone series. Levonorgestrel-oxime-17-acetate has been on the OC market for some years as a combination preparation with ethinylestradiol (DE 16 18 752, DE 16 20 102, DE 26 33 210, U.S. Pat. No. 3,780,073, U.S. Pat. No. 4,027,019, all Ortho Pharmaceutical Corp.).

Pharmacologically active 3-oximes and O-acylates of steroid-spirolactones have not been described to date; only 3-hydroxyimino-5β,17α-pregnane-21,17-carbolactone is described in DE 43 21 937 as an intermediate compound for the production of the corresponding 3-amino compound that is suitable for treatment of latent and manifest heart failure.

The object of the invention is also the process for the production of the compounds of formula I.

The production of the compounds of formula I is characterized in that the compound of formula II (drospirenone)

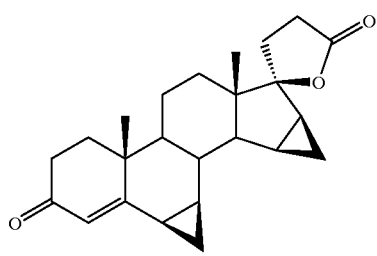

(II)

is converted into 3-hydroxyimino compounds and the latter are then optionally reacted by esterification with a carboxylic anhydride [(R'C(O)]$_2$O or an acid halide R'C(O)X (X=Cl, Br; R' has the meaning indicated in general formula I) in the presence of a base into the 3-acyloxyimino compounds.

The oxime of general formula I (i.e., R=H) is produced in the reaction of drospirenone with hydroxylamine-hydrochloride/pyridine as an (E,Z)-mixture with an (E,Z) ratio≈4:1.

By reaction with the corresponding acid anhydride or acid halide in the presence of pyridine, optionally with the addition of dimethylaminopyridine, the (E,Z)-mixture of oxime is converted into the acyloxyimino compounds [i.e., R=C(O)R'] of general formula I.

The C=N double bond that is contained in the compounds of formula I gives rise to the production of geometric isomers in the form of (E,Z)-mixtures, which can be separated chromatographically into pure (E) and (Z) isomers.

The compounds according to the invention are extremely active gestagens, which are suitable for maintaining pregnancies when administered transdermally, parenterally, as well as orally. In combination with an estrogen, combination preparations can be obtained that can be used for contraception and with menopausal symptoms.

Owing to their high gestagenic activity, the new compounds of general formula (I) can be used, for example, by themselves or in combination with estrogens in preparations for contraception. The new compounds, however, also open all other possible uses that are now known for gestagens (see, e.g., "Kontrazeption mit Hormonen [Contraception with Hormones]," Hans-Dieter Taubert and Herbert Kuhl, Georg Thieme Verlag Stuttgart—New York, 1995).

The dosage of the active ingredients can vary depending on the method of administration, age and weight of the patient, the desired indication, as well as the type and severity of the disease to be treated and similar factors. The daily dose is 0.1–25 mg, preferably 0.5–5 mg, whereby the dose can be given as a single dose to be administered once or divided into two or more daily doses. In the case of the transdermal systems, up to 14 daily doses can also be given in sequence by a system. In the case of implants, intravaginal systems, such as, e.g., a vaginal ring and intrauterine systems, such as, e.g., mirena, the active ingredients may be administered over a period of up to 3 years.

The gestagenic and estrogenic active ingredient components are preferably administered together in contraception preparations. In the case of oral administration, the daily dose is preferably administered one time.

As estrogens, all natural and synthetic compounds that are known to be estrogenically active are suitable.

As natural estrogens, these are especially estradiol and also its longer-acting esters, such as valerate, etc., or estriol.

As synthetic estrogens, ethinylestradiol, 14α,17α-ethano-1,3,5(10)-estratriene-3,17β-diol (WO 88/01275), 14α,17α-ethano-1,3,5(10)-estratriene-3,16α,17β-triol (WO 91/08219) or the 15,15-dialkyl derivatives of estradiol and of these especially the 15,15-dimethylestradiol can be mentioned. Ethinylestradiol is preferred as a synthetic estrogen.

The estratrien-3-amidosulfonates that recently became known (WO 96/05216 and WO 96/05217), derived from estradiol or ethinylestradiol, which are distinguished by low hapatic estrogeneity, are also suitable as estrogens for use together with the compounds of general formula I. Finally, the 14α,15α-methylene steroids from the estrane series (U.S. Pat. No. 4,231,946), especially 14α,15α-methylene-17α-estradiol, as well as the corresponding ester derivatives (WO 95/01988), can also be mentioned.

The estrogen is administered in an amount that corresponds to that of 0.01 to 0.05 mg of ethinylestradiol.

The new compounds of general formula (I) can also be used in preparations for treating gynecological disorders and for substitution therapy.

Finally, the new compounds can also be used as gestagenic components in the compositions that have recently become known for female birth control, which are distinguished by the additional use of a competitive progesterone antagonist (H. B. Croxatto and A. M. Salvatierra in Female Contraception and Male Fertility Regulation, ed. by Runnebaum, Rabe & Kiesel—Vol. 2, Advances in Gynecological and Obstetric Research Series, Parthenon Publishing Group—1991, page 245).

The dosage is in the already indicated range above, and formulation can be done as in conventional OC preparations. The administration of additional competitive progesterone antagonists can also be done sequentially in this case.

For transdermal administration, especially transdermal systems based on the matrix or membrane principle, as well as semisolid and liquid preparations such as oleogels or hydrogels, are suitable.

For the production of transdermal systems, skin contact adhesives, such as, e.g., polyacrylates, silicone adhesives, synthetic rubbers such as polyisobutylene as well as films, such as, e.g., polyethylene, polypropylene, ethylene vinyl acetate, polyvinyl chloride, polyvinylidene chloride, polyester as well as removable protective films made of, e.g., polyester or paper, which are siliconized on one or both sides or are fluoropolymer-coated are suitable.

For the production of transdermal solutions and gels, water and organic solvents as well as their mixtures are suitable. Gels can be thickened by incorporating suitable gel formers such as, e.g., silicon dioxide, tragacanth gum, starch and its derivatives, cellulose and its derivatives or polyacrylic acid and its derivatives.

The formulation of the compounds of general formula I in a transdermal system can be done analogously to the formulation of 3-ketodesogestrel that is described in WO 94/04157.

For possible configuration of transdermal systems into which the compounds of general formula I can be incorporated, please refer to, for example, the following basic bibliographic references: Barry, B. W., "Dermatological Formulations, Percutaneous Absorption"; Marcel Dekker, Inc., New York—Basel, 1983 as well as Chien, Y. W., "Transdermal Controlled Systemic Medications," Marcel Dekker, Inc., New York—Basel, 1987.

For the production of implants or pharmaceutical substance-laden intravaginal systems (e.g., vaginal rings) or intrauterine systems (e.g., pessaries, spirals), various polymers, such as, for example, silicone polymers, ethylene vinyl acetate, polyethylene, and polypropylene are suitable.

Pharmaceutical preparations that contain compounds of general formula I are produced according to usual processes, by the active ingredient being put by suitable vehicles, adjuvants, and/or additives into the form of a pharmaceutical preparation that is suitable for enteral or parenteral administration. The preparations that are thus obtained can be used as pharmaceutical agents in human or veterinary medicine. Administration may be done orally or sublingually as a solid in the form of capsules or tablets or as a liquid in the form of solutions, suspensions, elixirs, aerosols, or emulsions or rectally in the form of suppositories or in the form of injection solutions that can optionally be administered also subcutaneously, intramuscularly or intravenously or by implant, or topically or intrathekally or transdermally, or by means of intrauterine pessaries. As adjuvants for the desired pharmaceutical agent formulation, the inert organic and inorganic media that are known to one skilled in the art are suitable, such as, e.g, water, gelatin, gum arabic, lactose, starch, magnesium stearate, talc, silicone polymers, polyacrylates, vegetable oils, polyalkylene glycols, etc. Moreover, preservatives, stabilizers, wetting agents, emulsifiers, or salts for altering osmotic pressure or buffers may optionally be contained.

The pharmaceutical preparations can come in solid form as, e.g., tablets, coated tablets, suppositories, capsules, implants, intravaginal systems, intrauterine systems, transdermal systems or in liquid form, e.g., as solutions, suspensions, or emulsions.

As vehicle systems, near-interface adjuvants such as salts, bile acids, or animal or vegetable phospholipids and their mixtures as well as liposomes or their components can also be used.

For oral use, especially tablets, coated tablets, or capsules with talc and/or hydrocarbon vehicles or binders, such as, e.g., lactose, corn, or potato starch, are suitable.

The following examples are used for a more detailed explanation of the invention:

EXAMPLE 1

3-Hydroxyimino-6β,7β;15β,16β-dimethylene-17α-pregn-4-ene-21,17-carbolactone

A. A solution of 10.0 g of 3-oxo-6β,7β;15β,16β-dimethylene-17α-pregn-4-ene-21,17-carbolactone in 75 ml of pyridine is mixed with 3.15 g of hydroxylammonium chloride and heated for one hour in a steam bath. The reaction mixture is stirred into ice water, the settled precipitate is filtered off, washed several times with water and dissolved in dichloromethane. The solution is dried on sodium sulfate, and the solvent is evaporated in a vacuum. The crystalline residue consists of 8.91 g of (E,Z)-3-hydroxy-imino-6β,7β;15β,16β-dimethylene-17α-pregn-4-ene-21,17-carbolactone, with an (E,Z)-ratio of 4:1, melting point 194° C., $[\alpha]_D$=174° (CHCl$_3$).

B. 2.0 g of (E,Z)-3-hydroxyimino-6β,7β;15β,16β-dimethylene-17α-pregn-4-ene-21,17-carbolactone is chromatographed on a silica gel column (Kromasil 100/10 μm) with a hexane-ethyl acetate mixture (7:3). 940 mg of (E)-3-hydroxyimino-6β,7β;15β,16β-dimethylene-17α-pregn-4-ene-21,17-carbolactone, melting point 244° C., and 330 mg of (Z)-3-hydroxyimino-6β,7β;15β,16β-dimethylene-17α-pregn-4-ene-21,17-carbolactone, melting point 156° C., is eluted.

EXAMPLE 2

3-Acetoxyimino-6β,7β;15β,16β-dimethylene-17α-pregn-4-ene-21,17-carbolactone

A. A solution of 3.0 g of (E,Z)-3-hydroxyimino-6β,7β;15β,16β-dimethylene-17α-pregn-4-ene-21,17-carbolactone, (E,Z)-ratio 4:1, in 15 ml of pyridine is mixed with 7.5 ml of acetic anhydride and stirred for 3 hours at room temperature. The reaction mixture is stirred into ice water, the settled precipitate is filtered off, washed several times with water and dissolved in dichloromethane. The solution is dried on sodium sulfate, and the solvent is evaporated in a vacuum. 3.21 g of (E,Z)-3-acetoxyimino-6β,7β;15β,16β-dimethylene-17α-pregn-4-ene-21,17-carbolactone, melting point 212° C., $[\alpha]_D$=−187° (CHCl$_3$) is obtained as a crystalline residue.

B. 960 mg of (E,Z)-3-acetoxyimino-6β,7β;15β,16β-dimethylene-17α-pregn-4-ene-21,17-carbolactone is chromatographed on a silica gel column (Kromasil 100/10 μm) with a hexane-ethyl acetate mixture (7:3). 531 mg of (E)-3-acetoxyimino-6β,7β;15β,16β-dimethylene-17α-pregn-4-ene-21,17-carbolactone, melting point 225° C., $[\alpha]_D$=−195° (CHCl$_3$), and 227 mg of (Z)-3-acetoxyimino-6β,7β;15β,16β-dimethylene-17α-pregn-4-ene-21,17-carbolactone, melting point 230° C., $[\alpha]_D$=−152° (CHCl$_3$), are eluted.

EXAMPLE 3

3-Propionyloxyimino-6β,7β;15β,16β-dimethylene-17α-pregn-4-ene-21,17-carbolactone A solution of 6.0 g of (E,Z)-3-hydroxyimino-6β,7β;15β,16β-dimethylene-17α-pregn-4-ene-21,17-carbolactone, (E,Z)-ratio=4:1, in 30 ml of pyridine is mixed with 15 ml of propionic acid anhydride and held at room temperature for 15 hours. The reaction mixture is poured into ice water and stirred for 2 hours, the settled precipitate is filtered off, washed several times with water and dissolved in dichloromethane. The solution is dried on sodium sulfate, and the solvent is evaporated in a vacuum. 6.85 g of crystalline (E,Z)-3-propionoyloxyimino-6β,7β;15β,16β-dimethylene-17α-pregn-4-ene-21,17-carbolactone, melting point 172° C., $[\alpha]_D$=−180° (CHCl$_3$), is obtained as a residue.

EXAMPLE 4

3-Butyryloxyimino-6β,7β;15β,16β-dimethylene-17α-pregn-4-ene-21,17-carbolactone A solution of 6.0 g of (E,Z)-3-hydroxyimino-6β,7β;15β,16β-dimethylene-17α-pregn-4-ene-21,17-carbolactone, (E,Z)-ratio 4:1, in 30 ml of pyridine is mixed with 15 ml of butyric acid anhydride and held at-room temperature for 16 hours. The reaction mixture is poured into ice water, stirred for 3 hours and the oily phase that precipitates is dissolved in dichloromethane. The solution is washed several times with water, dried on sodium sulfate, and the solvent is evaporated in a vacuum. 5.7 g of crystalline (E,Z)-3-butyryloxyimino-6β,7β;15β,16β-dimethylene-17α-pregn-4-ene-21,17-carbolactone, melting point 142° C., $[\alpha]_D=-179°$ (CHCl$_3$), is obtained as a residue.

EXAMPLE 5

3-Hexanoyloxyimino-6β,7β;15β,16β-dimethylene-17α-pregn-4-ene-21,17-carbolactone A solution of 4.4 g of (E,Z)-3-hydroxyimino-6β,7β;15β,16β-dimethylene-17α-pregn-4-ene-21,17-carbolactone, (E,Z)-ratio 4:1, in 30 ml of pyridine is mixed with 15 ml of caproic acid anhydride as well as 500 mg of 4-dimethylaminopyridine and heated for two hours to 60° C. The reaction mixture is poured into ice water, stirred for 15 hours, and the oily product that precipitates is dissolved in dichloromethane. The solution is washed several times with water, dried on sodium sulfate, and the solvent is evaporated in a vacuum. The residue of 6.13 g is chromatographed on a silica gel column (Kromasil 100/10 μm) with a hexane-ethyl acetate mixture (7:3). 5.6 g of (E,Z)-3-hexanoyloxyimino-6β,7β;15β,16β-dimethylene-17α-pregn-4-ene-21,17-carbolactone in the form of a pale yellow oil, $[\alpha]_D=-143°$ (CHCl$_3$), as well as 1.32 g of (E)-3-hexanoyloxyimino-6β,7β;15β,16β-dimethylene-17α-pregn-4-ene-21,17-carbolactone are eluted as foam, $[\alpha]_D-171°$ (CHCl$_3$), and 0.33 g of (Z)-3-hexanoyloxyimino-6β,7β;15β,16β-dimethylene-pregn-4-ene-21,17-carbolactone is eluted as foam, $[\alpha]_D=-130°$ (CHCl$_3$).

EXAMPLE 6

3-Nonanoyloxyimino-6β,7β;15β,16β-dimethylene-17α-pregn-4-ene-21,17-carbolactone A solution of 5.7 g of (E,Z)-3-hydroxyimino-6β,7β;15β,16β-dimethylene-17α-pregn-4-ene-21,17-carbolactone in 30 ml of pyridine is mixed with 5 ml of nonanoic acid anhydride and heated for 30 minutes in a steam bath. The reaction mixture is stirred into ice water, the oily product is isolated after 30 minutes and taken up in dichloromethane. The solution is washed several times with water, dried on sodium sulfate, and the solvent is evaporated in a vacuum. The residue is chromatographed on a silica gel column with a hexane-ethyl acetate mixture (7:3). 7.8 g of (E,Z)-3-nonanoyloxyimino-6β,7β;15β,16β-dimethylene-17α-pregn-4-ene-21,17-carbolactone in the form of a pale yellow oil, $[\alpha]_D=-128°$ (CHCl$_3$), is eluted.

We claim:
1. A compound of formula I,

(I)

wherein R means a hydrogen atom or an acyl radical with 2 to 10 C atoms.

2. A compound according to claim 1,
   wherein R is a hydrogen atom.
3. A compound according to claim 1,
   wherein R is C(O)R',
   wherein R' is a hydrocarbon radical that is straight-chain, branched-chain or cyclic, saturated or unsaturated in up to three places; an alkylcycloalkyl or cycloalkenyl radical, in each case with up to 9 carbon atoms; or a benzoyl radical.
4. A compound according to claim 3, wherein R' is a straight-chain saturated hydrocarbon radical with 1 to 9 carbon atoms.
5. A compound according claim 1 selected from
   (E,Z)-3-Hydroxyimino-6β,7β;15β,16β-dimethylene-17α-pregn-4-ene-21,17-carbolactone;
   (E)-3-hydroxyimino-6β,7β;15β,16β-dimethylene-17α-pregn-4-ene-21,17-carbolactone;
   (Z)-3-hydroxyimino-6β,7β;15β,16β-dimethylene-17α-pregn-4-ene-21,17-carbolactone;
   (E,Z)-3-acetoxyimino-6β,7β;15β,16β-dimethylene-17α-pregn-4-ene-21,17-carbolactone;
   (E)-3-acetoxyimino-6β,7β;15β,16β-dimethylene-17α-pregn-4-ene-21,17-carbolactone;
   (Z)-3-acetoxyimino-6β,7β;15β,16β-dimethylene-17α-pregn-4-ene-21,17-carbolactone;
   (E,Z)-3-propionyloxyimino-6β,7β;15β,16β-dimethylene-17α-pregn-4-ene-21,17-carbolactone;
   (E)-3-propionyloxyimino-6β,7β;15β,16β-dimethylene-17α-pregn-4-ene-21,17-carbolactone;
   (Z)-3-propionyloxyimino-6β,7β;15β,16β-dimethylene-17α-pregn4-ene-21,17-carbolactone;
   (E,Z)-3-butryryloxyniino-6β,7β;15β,16β-dimethylene-17α-pregn-4-ene-21,17-carbolactone;
   (E)-3-butyryloxyimino-6β,7β;15β,16β-dimethylene-17α-pregn-4-ene-21,17-carbolactone;
   (Z)-3-butyryloxyimino-6β,7β;15β,16β-dimethylene-17α-pregn-4-ene-21,17-carbolactone;
   (E,Z)-3-hexanoyloxyimino-6β,7β;15β,16β-dimethylene-17α-pregn-4-ene-21,17-carbolactone;
   (E)-3-hexanoyloxyimino-6β,7β;15β,16β-dimethylene-17α-pregn-4-ene-21,17-carbolactone;
   (Z)-3-hexanoyloxyimino-6β,7β;15β,16β-dimethylene-17α-pregn4-ene-21,17-carbolactone;
   (E,Z)-3-nonanoyloxyimino-6β,7β;15β,16β-dimethylene-17α-pregn-4-ene-21,17-carbolactone;
   (E)-3-nonanoyloxyimino-6β,7β;15β,16β-dimethylene-17α-pregn-4-ene-21,17-carbolactone; or (,Z)-3-nonanoyloxyimino-6β,7β;15β,16β-dimethylene-17α-pregn-4-ene-21,17-carbolactone.

6. A compound according to claim 1 in the form of an E,Z-mixture.

7. A compound according to claim 1 in the form of a substantially pure E-isomer.

8. A compound according to claim 1 in the form of a substantially pure Z-isomer.

9. A compound according to claim 1, wherein R is C2–C10 alkanoyl.

10. A compound according to claim 1, wherein R is C(O)R', wherein R' is a methyl group, an ethyl group, a propyl group, a butyl group, a pentyl group, a hexyl group, a heptyl group, an octyl group or a nonyl group.

11. A composition comprising a compound according to claim 1 and a pharmacologically compatible vehicle.

12. A composition comprising a compound according to claim 1 and one or more estrogens.

13. A contraceptive formulation comprising a composition according to claim 12, wherein the composition is formulated to provide a daily dose of 0.1–25 mg of the compound.

14. A method of treating endometriosis, a gestagen-dependent tumor, premenstrual syndrome, a menopausal symptom, or osteoporosis comprising administering, to a subject in need thereof, a compound according to claim 1.

15. A method of birth control, comprising administering, to a subject in need thereof, a compound according to claim 1.

16. A method of birth control according to claim 15, further comprising administering one or more estrogens.

17. A method of cycle regulation or cycle stabilization, in a female mammal in need thereof, comprising administering a compound according to claim 1.

18. A method of maintaining a pregnancy, in a female mammal in need thereof, comprising administering a compound according to claim 1.

19. A method according to claim 14, wherein the compound is administered in a daily dose amount of 0.1–25 mg.

20. A method according to claim 15, wherein the compound is administered in a daily dose amount of 0.1–25 mg.

21. A method according to claim 16, wherein the estrogen is administered in a daily dose amount that corresponds to 0.01–0.05 mg of ethinylestradiol.

22. A process for the production of compounds according to claim 1, wherein the compound of formula II

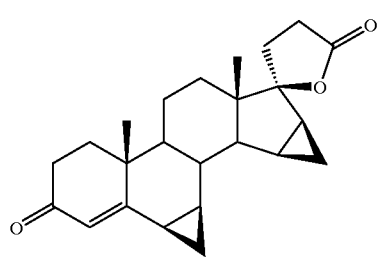

is converted into the 3-hydroxyimino compound and optionally the latter then is reacted by esterification with a carboxylic anhydride [R'C(O)]$_2$O or an acid halide R'C(O)X, wherein X is Cl or Br, in the presence of a base into the 3-acyloxyimino compound;

wherein R' is a hydrocarbon radical that is straight-chain or branched-chain or cyclic, saturated or unsaturated in up to three places; an alkylcycloalkyl or cycloalkenyl radical, in each case with up to 9 carbon atoms; or a benzoyl radical.

23. A process according to claim 22, wherein R' is a straight-chain saturated hydrocarbon radical with 1 to 9 carbon atoms.

* * * * *

UNITED STATES PATENT AND TRADEMARK OFFICE
CERTIFICATE OF CORRECTION

PATENT NO. : 6,177,416 B1
DATED : January 23, 2001
INVENTOR(S) : Laurent et al.

It is certified that error appears in the above-identified patent and that said Letters Patent is hereby corrected as shown below:

<u>Column 8,</u>
Line 51, reads "(E,Z)-3-butryryloxyniino-" should read -- (E,Z)-3-butryryloxyimino --

Signed and Sealed this

Fifth Day of February, 2002

Attest:

Attesting Officer

JAMES E. ROGAN
*Director of the United States Patent and Trademark Office*